United States Patent [19]

Chan et al.

[11] Patent Number: 4,611,082

[45] Date of Patent: Sep. 9, 1986

[54] PRODUCTION OF HEX-3-ENEDIOATE ESTERS FROM 1,4 DIALKOXY BUTENES

[75] Inventors: Albert S. C. Chan, St. Charles; Donald E. Morris, Kirkwood, both of Mo.

[73] Assignee: Monsanto Company, St. Louis, Mo.

[21] Appl. No.: 669,720

[22] Filed: Nov. 9, 1984

[51] Int. Cl.$^4$ .............................................. C07C 67/37
[52] U.S. Cl. .................................... 560/204; 502/229; 502/230; 562/592
[58] Field of Search ...................... 560/204; 562/592; 502/229, 230

[56] References Cited

U.S. PATENT DOCUMENTS

| | | | |
|---|---|---|---|
| 2,542,767 | 2/1951 | Gresham et al. | 560/204 X |
| 4,102,920 | 7/1978 | Bartish | 560/204 X |
| 4,166,913 | 9/1979 | Kesling et al. | 560/204 |
| 4,169,956 | 10/1979 | Kummer et al. | 560/204 |
| 4,171,450 | 10/1979 | Kesling et al. | 560/204 |
| 4,171,451 | 10/1979 | Kummer et al. | 560/204 |
| 4,189,599 | 2/1980 | Kesling et al. | 560/190 |

OTHER PUBLICATIONS

Imamura et al., *Tetrahedron*, vol. 25, pp. 4187-4195, (1969).

*Primary Examiner*—Natalie Trousof
*Assistant Examiner*—Vera C. Clarke
*Attorney, Agent, or Firm*—Thomas N. Wallin

[57] ABSTRACT

The dicarbonylation product of 1,4-dialkoxy substituted-2-butene is useful as intermediate in the production of adipic acid, hexamethylenediamine and 1,6-hexanediol. It is produced by carbonylating a solution of the dialkoxy substituted butene in a polar, aprotic nonbasic solvent at 80°-140° C. in the presence of a catalyst comprising a halide of the transition metal.

17 Claims, No Drawings

PRODUCTION OF HEX-3-ENEDIOATE ESTERS FROM 1,4 DIALKOXY BUTENES

BACKGROUND OF THE INVENTION

A. Field of the Invention

The invention relates to the production of hex-3-enedioate esters, and more particularly to the production of dialkyl hex-3-enedioate, an intermediate used in the production of adipic acid, from substituted butenes such as 1,4-dialkoxy-2-butene.

Adipic acid is produced at a worldwide capacity of nearly five billion pounds, most of which is used as a raw material for nylon 66 polymer production. Adipic acid is produced commercially by the air oxidation of cyclohexane to a cyclohexanone/cyclohexanol mixture (KA oil) which is subsequently oxidized to adipic acid with nitric acid. Adipic acid is also produced commercially from phenol by hydrogenation to cyclohexanol, the cyclohexanol being subsequently oxidized with nitric acid to adipic acid. Although adipic acid has been so produced for nearly forty (40) years, there are two major disadvantages in the current commercial processes. The air oxidation of cyclohexane must be carried out at low conversion rates in order to achieve high selectivity; and the recycling of large amounts of cyclohexane is potentially hazardous. Benzene which is the hydrocarbon source, is not expected to continue to be a low cost material.

U.S. Pat. No. 4,166,913 to ARCO describes production of adipic acid from carbon monoxide and butadiene. The ARCO process can be summarized by the following equations:

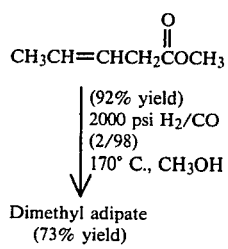

$$CH_2=CH-CH=CH_2 + 2CO + \tfrac{1}{2}O_2 + CH_3OH +$$

$$\downarrow \begin{array}{l} PdCl_2, LiCl, CuCl_2 \\ 130 \text{ atm CO, 7 atm } O_2, 100^\circ \text{ C.} \end{array}$$

$$\underset{\substack{\text{O} \\ \|}}{CH_3O\overset{}{C}CH_2CH}=CHCH_2\underset{\substack{\| \\ \text{O}}}{\overset{}{C}OCH_3} + \text{cyclohexanone}$$

(52% conversion, 86% selectivity, based on butadiene)

$$\downarrow \begin{array}{l} 13 \text{ atm } H_2, \\ 50^\circ \text{ C., Pd/C} \end{array}$$

Dimethyl adipate (94% yield)

$$\downarrow H_2O, H^+$$

Adipic Acid

The need for dehydrating agents and the potential safety hazard of the high pressure CO/O₂ mixture under catalytic reaction conditions are significant disadvantages in the practice of the above production method.

A second known alternative to the production of adipic acid is described in U.S. Pat. Nos. 4,169,956 and 4,171,451 to BASF. The process can be summarized schematically as follows:

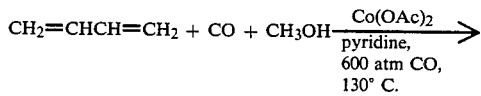

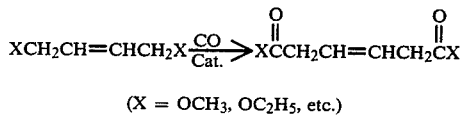

$$\downarrow \begin{array}{l} 2000 \text{ psi } H_2/CO \\ (2/98) \\ 170^\circ \text{ C., } CH_3OH \end{array}$$

Dimethyl adipate
(73% yield)

A major disadvantage in this process is the extremely high reaction pressure required in the carbonylation step.

Previous attempts to dicarbonylate 1,4-disubstituted-2-butenes have been relatively unsuccessful. In the attempt described by Medema, D.; van Helden, R.,; Kohll, C. F. *Inorg. Chim. Acta.*, 3 (1969) 155, page 20, it was reported that only 3% of 3-pentenoyl chloride was obtained in the attempt to dicarbonylate 1,4-dichloro-2-butene. No dicarbonylated product was observed. In the dicarbonylation attempt described by Imamura, S.; Tsuji, J.; *Tetrahedron* 25 (1969) 4187, it was observed that only about 10–37% of linear dicarbonylated products were obtained in a palladium chloride-catalyzed carbonylation of 1,4-diethoxy-2-butene; and that large amounts of by-products resulted from isomerization and hydrogenolysis of the starting material or reaction intermediates.

If a method for the production of an intermediate of adipic acid could be found based on the less expensive butenes, or derivatives thereof, without the problems of hydrogenolysis and isomerization described above, such a method would be a significant advance in the art and is an object of this invention.

SUMMARY OF THE INVENTION

According to this invention, hex-3-enedioate esters such as dialkyl hex-3-enedioate are produced by carbonylating a solution of substituted butenes such as 1,4-dialkoxy-2-butene, in an aprotic, polar non-basic solvent, in the presence of a catalyst comprising a halide of a transition metal. The dialkyl hex-3-enedioate esters can be converted to adipic acid and by hydrogenation and hydrolysis essentially as described above in the last two steps shown as part of the process described in U.S. Pat. No. 4,166,913, hereby incorporated by reference.

DETAILED DESCRIPTION OF THE INVENTION

The catalytic dicarbonylation of 1,4-dialkoxy-2-butene is shown as follows:

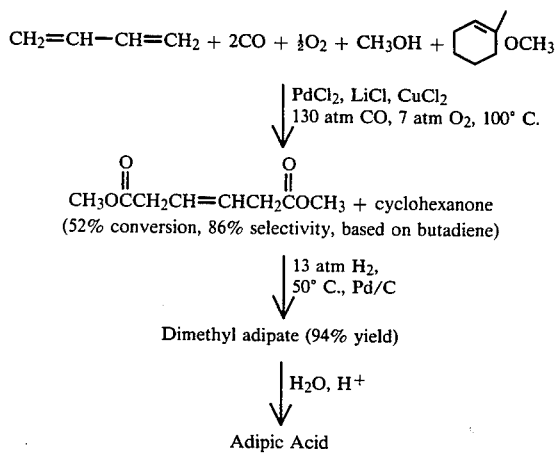

(X = OCH₃, OC₂H₅, etc.)

The catalyst may be any transition metal halide, but palladium chloride is preferred. Other palladium halides such as palladium bromide and, to a lesser extent, palladium iodide have been found to be effective but to a much lower yield than the palladium chloride. Other transition metal salts such as nickel chloride have also been found to be effective but to a much lower yield than palladium chloride.

As indicated above, the hex-3-enedioate esters are produced by carbonylating a solution of substituted butenes in an aprotic, polar non-basic solvent, and heating the solution in the presence of a catalyst comprising a halide of a transition metal.

Polar, aprotic, non-basic solvents are required for high catalyst activity and high selectivity to the desired linear dicarbonylated products. Solvents of high polarity are required in order to maintain the solubility of the metal catalyst and thus high catalyst activity; aprotic solvents are necessary in order to obtain high selectivity to the linear dicarbonylated product. The presence of protic solvents causes isomerization and hydrogenolysis products. The presence of solvents which are too basic results in poorly active or inactive catalysts. Suitable solvents are known to include nitriles such as benzonitrile, propionitrile, isobutyronitrile, acetonitrile, and trimethylacetonitrile. Dipolar, aprotic, non-basic solvents of similar donor properties to those of the nitriles, such as bis(2-methoxyethyl)ether (diglyme), methylene chloride, and 1,4-dimethoxy-2-butene will also serve suitably as a solvent in the reaction. Other solvents expected to fall in this category include nitrobenzene, nitromethane, ketones and the like. When aprotic, relatively poor alpha-donor solvents such as carbon tetrachloride, toluene, and benzene were employed, very little reaction was observed. For example, only 55% substrate conversion was obtained when the reaction was attempted in toluene. This may be compared to the 90 to 100% substrate conversisons obtained when the reaction is run in the preferred solvents mentioned above. When polar, aprotic, but more basic solvents such as N,N-disubstituted-amides were employed, again low conversions are obtained. For example, only 8% substrate conversion was obtained when the reaction was attempted in N,N-dimethylformamide. When polar, non-basic, but protic solvents such as alcohols are employed low selectivities to the desired linear dicarbonylated products are obtained (see Example 4). A comparison of solvent systems is shown in Table 1, where the carbonylation reaction was conducted as in Example I except as otherwise noted.

tures. Reaction temperatures of about 80°–140° C. has been found to be suitable for the compromise of rates and selectivity. Lewis acids have been found to significantly increase the rates of reaction, but at some sacrifice of selectivity.

The substituents on the 1,4-dialkoxy-2-butenes are an important factor in determining the amount of yield. Although allyl chloride has been found to be the most easily carbonylated allylic species, and high yields of the carbonylation product have been achieved, low yields of dicarbonylation products have been obtained in attempts to dicarbonylate 1,4-dichloro-2-butenes. Carbonylation of 2-butene-1,4-diol is excellent, but the compound decomposes under reaction conditions and so the yields of the linear dicarbonylation products are not high. 1,4-diacetoxy-2-butene is almost inert towards carbonylation, but in the presence of an alcohol, the rates increase so as to be comparable to those for the carbonylation of 2-butene-1,4-diol. The highest yields have been found for the carbonylation of 1,4-dimethoxy-2-butene, and other 1,4-dialkoxy-2-butene substrates.

EXAMPLES

Example 1

A 300 ml Hastelloy B autoclave equipped with a Magnedrive stirrer was charged with 0.44 g $PdCl_2$ (2.5 mmol), 2.6 g 1,4-dimethoxy-2-butenes (over 90% trans, 22.4 mmol) and 70 g isobutyronitrile solvent. The solution was heated under 2500 psig CO to 100° C. The reaction was allowed to proceed for 20 hours at 100° C. under 199 atm CO. G.C. analyses of the final solution indicated over 99% conversion of 1,4-dimethoxy-2-butenes. 72% yield of dimethyl-3-hexenedioate

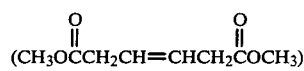
$$(CH_3OCCH_2CH=CHCH_2COCH_3)$$

and 15% yield of

TABLE 1

Comparison of Solvent Systems for the $PdCl_2$—Catalyzed Carbonylation of 1,4-Dimethoxy-2-butene

| Solvent | Reaction Time (hours) | % Conversion | % Yield of $CH_3CH=CHCH_2CO_2CH_3$ (cis + trans) | % Yield of $CH_3OCHCH_2CH=CHCH_2CO_2CH_3$ (cis + trans) | % Yield of $CH_3O_2CCH_2CH=CHCH_2CO_2CH_3$ (cis + trans) |
|---|---|---|---|---|---|
| $C_6H_5CN$ | 24 | 100 | 3 | 3 | 78 |
| $CH_3CN$ | 20 | 94 | 3 | 41 | 33 |
| $(CH_3)_2CHCN$ | 20 | 92 | 4 | 48 | 33 |
| Diglyme | 22.5 | 91 | 6 | 55 | 35 |
| $CH_2Cl_2$ | 22 | 100 | 2 | 4 | 74 |
| Toluene | 23.5 | 55 | 2 | 31 | 2 |
| DMF | 24 | 8 | — | 1 | 0 |
| HMPA | 24 | | Virtually no reaction | | |
| $DM_2$-$B^b$ | 48 | 91 | <1 | 57 | 25 |

$^a$[Pdcl$_2$] = 2.5 × 10$^{-2}$ M; [CH$_3$OCH$_2$CHCHCH$_2$OCH$_3$] = 1 M; Pco = 199 atm; T = 100° C. DMF = nin-dimethylformamide; HMPA = hexamethylphosphoramide; DM-2-B = 1,4-dimethoxy-2-butene.
$^b$The substrate is also solvent. [CH$_3$OCH$_2$CHCHCH$_2$OCH$_3$] = 7.9 M.

In order to optimize the rates and selectivity for the dicarbonylation of 1,4-dimethoxy-2-butene, the temperature dependence of this reaction has been studied. As expected, the reaction rates increase with the increase of reaction temperature. However the starting material begins to decompose and polymerize at higher temperatures. Catalyst deactivation via precipitation of palladium metal is also more severe at the higher tempera-

were obtained.

Example 2

Same as example 1 except that the materials charged were 0.44 g PdCl$_2$ (2.5 mmol), 2.5 g CuCl (25 mmol), 7.5 g 1,4-dimethoxy-2-butenes (over 90% trans, 65 mmol), and 67.5 g acetonitrile solvent. G.C. analyses of the final product after 21 hours of reaction indicated over 99% conversion of 1,4-dimethoxy-2-butenes. 71% yield of diemethyl-3-hexenedioate

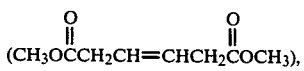
(CH$_3$OCCH$_2$CH=CHCH$_2$COCH$_3$),

9% yield of

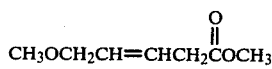
CH$_3$OCH$_2$CH=CHCH$_2$COCH$_3$ and 7% yield of

CH$_3$CH=CHCH$_2$COCH$_3$ were observed.

Example 3

Same as 1 except that the materials charged were 0.44 g PdCl$_2$ (2.5 mmol), 12.2 g 1,4-dimethoxy-2-butene (over 90% cis, 105 mmol), and 86.3 g benzonitrile (solvent). G.C. analyses of the products after 24 hours indicated over 99% conversion of 1,4-dimethoxy-2-butene. 78% yield of

CH$_3$OCCH$_2$CH=CHCH$_2$COCH$_3$

3% yield of

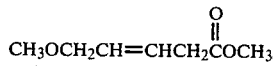
CH$_3$OCH$_2$CH=CHCH$_2$COCH$_3$ and 3% yield of

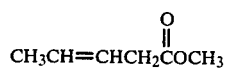
CH$_3$CH=CHCH$_2$COCH$_3$ were observed.

What is claimed is:

1. A process for the production of dialkyl hex-3-enedioate esters from 1,4-dialkoxy substituted-2-butenes comprising carbonylating a solution of the substituted butene in an aprotic, polar non-basic solvent selected from the group consisting of nitriles; bis(2-methoxy-2-butene; bis(2-methoxyethyl)ether; and methylene chloride at 80°–140° C. in the presence of a catalyst comprising a halide of a transition metal.
2. The process of claim 1 wherein the 1,4-disubstituted-2-butene is 1,4-dimethoxy-2-butene.
3. The process of claim 1 wherein the solvent is a nitrile.
4. The process of claim 1 wherein the solvent is benzonitrile.
5. The process of claim 1 wherein the solvent is propionitrile.
6. The process of claim 1 wherein the solvent is isobutyronitrile.
7. The process of claim 1 wherein the solvent is acetonitrile.
8. The process of claim 1 wherein the solvent is trimethylacetonitrile.
9. The process of claim 1 wherein the solvent is bis(2-methoxyethyl)ether.
10. The process of claim 1 wherein the solvent is methylene chloride.
11. The process of claim 1 wherein the catalyst is a palladium dihalide.
12. The process of claim 11 wherein the catalyst is palladium dichloride.
13. The process of claim 11 wherein the catalyst is palladium diiodide.
14. The process of claim 11 wherein the catalyst is palladium dibromide.
15. The process of claim 1 wherein the catalyst is nickel dichloride.
16. The process of claim 11 wherein the catalyst is formed in situ.
17. The process of claim 1 conducted in the presence of minor amounts of a Lewis acid.

* * * * *